(12) United States Patent
Boruch (10) Patent No.: US 8,685,634 B2
(45) Date of Patent: Apr. 1, 2014

(54) NEURAL SCAFFOLDS

(75) Inventor: Alan V. Boruch, Pittsburgh, PA (US)

(73) Assignee: University of Pittsburgh—Of the Commonwealth System of Higher Education, Pittsburgh, PA (US)

( * ) Notice: Subject to any disclaimer, the term of this patent is extended or adjusted under 35 U.S.C. 154(b) by 804 days.

(21) Appl. No.: 12/718,227

(22) Filed: Mar. 5, 2010

(65) Prior Publication Data

US 2010/0226895 A1  Sep. 9, 2010

Related U.S. Application Data (60) Provisional application No. 61/157,999, filed on Mar. 6, 2009.

(51) Int. Cl.
*C12N 5/00* (2006.01)

(52) U.S. Cl.
USPC ............ 435/1.1; 435/378; 424/570; 424/423

(58) Field of Classification Search
None
See application file for complete search history.

(56) References Cited

U.S. PATENT DOCUMENTS

| 6,448,076 | B2 | 9/2002 | Dennis et al. |
| 6,962,814 | B2 * | 11/2005 | Mitchell et al. ............... 435/402 |
| 7,402,319 | B2 | 7/2008 | Schmidt et al. |

FOREIGN PATENT DOCUMENTS

WO  2011072393 A1  6/2011

OTHER PUBLICATIONS

Yin et al, Nan fang yi ke da xue xue bao (Journal of Southern Medical University), Oct. 2008 vol. 28, No. 10, pp. 1748-1751. Abstract Only.*
Sondell et al, Brain Research, 1998, vol. 795, pp. 44-54.*
Yin et al, Nan fang yi ke da xue xue bao (Journal of Southern Medical University), Oct. 2008, vol. 28, No. 10, pp. 1748-1751. (Full translation).*
Gulati, Adarsh K., "Evaluation of acellular and cellular nerve grafts in repair of rat peripheral nerve", J Neurosurg., 1988, pp. 117-123, vol. 68.
Ribatti, Domenico et al., "Angiogenic response induced by acellular brain scaffolds grafted onto the chick embryo chorioallantoic membrane", Brain Research, 2003, pp. 9-15, vol. 989.

* cited by examiner

*Primary Examiner* — Allison Ford
(74) *Attorney, Agent, or Firm* — The Webb Law Firm (57) ABSTRACT

Disclosed herein are compositions and methods useful for preparing neural scaffolds. The scaffolds comprise tissue taken from the spinal cord and/or dura mater of vertebrate and can be processed to form gels or sheets. Methods of treating patient with CNS injury are also presented.

22 Claims, 8 Drawing Sheets

NEURAL SCAFFOLDS

CROSS-REFERENCE TO RELATED APPLICATION

This application claims the benefit of U.S. Provisional Patent Application Ser. No. 61/157,999, filed Mar. 6, 2009.

STATEMENT REGARDING FEDERAL FUNDING

The U.S. Government has a paid-up license in this invention and the right in limited circumstances to require the patent owner to license others on reasonable terms as provided for by the terms of Grant No. 5T32EB000424-05 awarded by the National Institutes of Health.

BACKGROUND OF THE INVENTION

Background

To date, no biocompatible scaffold has successfully engrafted with neural tissue. Thus, there is a significant clinical need for a method to support axonal sparing, remodeling and tissue regeneration within an injured spinal cord.

SUMMARY

Tissue scaffolds for neural tissue regeneration and replacement are disclosed herein. In certain embodiments, scaffolds are derived from spinal cord tissue that has been decellularized. Such decellularized neural scaffolds can be manufactured using enzymatic and chemical treatment protocols, for example, to remove cellular and extracellular materials from spinal cord tissue. In certain embodiments, the neural scaffolds are at least partially in a gel state. The gel properties of such scaffolds allow direct placement or injection into tissues, including the brain and spinal cord, to create a local niche/environment conducive to regeneration. According to certain embodiments, the scaffolds are biodegradable, elastomeric, porous and biocompatible.

In certain embodiments, neural scaffolds can be lyophilized for storage. In yet other embodiments, the scaffolds can be used as a sheet or made into a powder. In certain other embodiments, dehydrated neural scaffolds can be reconstituted as either a solution or a gel for use. In various embodiments, neural scaffolds can be sterilized using irradiation, ethylene oxide, or other methods.

In yet other embodiments, neural scaffolds can also be chemically to act as a drug delivery system at a site of neural injury or disease.

Neural scaffolds are particularly useful for inducing, supporting, and guiding the growth of neuronal cells into sites of neural disease or injury, such as in the central nervous system (CNS) and spinal cord. For example in one embodiment, a neural scaffold is grafted at, around or near a site in need of wound healing, tissue remodeling and/or tissue regeneration. In another non-limiting embodiment, such a scaffold comprises cells. For example and without limitation, such a method comprises culturing cells in and/or on a biodegradable elastomeric scaffold in vitro and implanting the scaffold. In yet another non-limiting embodiment, the biodegradable elastomeric scaffold comprises bioactive or therapeutic agents, such as, without limitation growth factors, antibiotics, and anti-inflammatory agents. For example, in certain embodiments, neural scaffolds can be seeded with stem/progenitor cells and/or ensheathing glia (such as olfactory ensheathing glia, oligodendrocyte lineage cells and Schwann cells).

BRIEF DESCRIPTION OF THE SEVERAL VIEWS OF THE DRAWINGS

The preferred embodiments of the present invention, illustrative of the best mode in which applicant has contemplated applying the principles, are set forth in the following description and are shown in the drawings, and are particularly and distinctly pointed out and set forth in the appended claims.

FIGS. 4A-4D are photomicrographs of acellular spinal cord parenchyma-derived scaffold.

FIGS. 5A-5B are scanning electron micrographs of acellular spinal cord parenchyma-derived scaffold.

FIGS. 6A-6C are photomicrographs of Masson's trichrome stained acellular spinal cord parenchyma-derived scaffold implanted with neuronal cells (PC 12). FIGS. 6A-6C show neuronal cell growth and migration into the scaffold, where neuronal cells (red, thin arrows) grow on and into the scaffold (blue, thick arrows). Photomicrographs are shown at the following magnifications: 100× (FIG. 6A), 200× (FIG. 6B), and 400× (FIG. 6C);

FIGS. 7A-7B are photomicrographs of Masson's trichrome stained acellular spinal cord parenchyma-derived scaffold implanted with neuronal cells (PC 12). FIGS. 7A-7B show neuronal cell growth and migration into the scaffold (blue, thick arrows), where neuronal cells grow on the surface of the spinal cord scaffold (red, thin arrows) and migration into the scaffold (arrowheads). Photomicrographs are shown at the following magnifications: 200× (FIG. 7A) and 400× (FIG. 7B); and FIGS. 8A-8D are photomicrographs of acellular dura mater-derived scaffold.

Similar numerals refer to similar parts throughout the drawings.

DETAILED DESCRIPTION OF THE INVENTION

Described herein are scaffolds suitable for use in tissue engineering and regenerative medicine applications, such as replacement of neural tissue. In certain embodiments, the scaffold comprises decellularized spinal cord tissue. Such tissue can be in a gel state. In another non-limiting embodiment, the scaffold comprises bioactive or therapeutic agents.

The use of numerical values in the various ranges specified in this application, unless expressly indicated otherwise, are stated as approximations as though the minimum and maximum values within the stated ranges are both preceded by the word "about". In this manner, slight variations above and below the stated ranges can be used to achieve substantially the same results as values within the ranges. Also, unless indicated otherwise, the disclosure of these ranges is intended as a continuous range including every value between the minimum and maximum values. For definitions provided herein, those definitions refer to word forms, cognates and grammatical variants of those words or phrases.

Scaffolds can be used for a large number of medical applications including, but not limited to, wound healing, tissue remodeling, and tissue regeneration. For example and without limitation, such scaffolds can be used for wound healing. In one non-limiting embodiment, the scaffold comprises bioactive agents to facilitate tissue healing, tissue remodeling and/or angiogenesis. In another non-limiting embodiment, the scaffold comprises bioactive agents to ward off bacteria and other pathogens. In yet another non-limiting embodiment, the scaffold comprises pores to allow a wound to drain. In yet another non-limiting embodiment, the scaffold comprises combinations of cells and bioactive agents. In another non-limiting embodiment, combinations of cells and bioactive agents are added to the scaffold before or during implantation at a site in a patient.

As used herein, the teen "polymer" refers to both synthetic polymeric components and biological polymeric components. The scaffolds described herein can comprise any suitable combination of synthetic polymeric components and biological polymeric components. "Biological polymer(s)" are polymers that can be obtained from biological sources, such as, without limitation, mammalian or vertebrate tissue, as in the case of certain extracellular matrix-derived (ECM-derived) compositions. As used herein the term "extracellular matrix" refers to any polymer remaining after decellularization included gels and solids. Biological polymers can be modified by additional processing steps. Polymer(s), in general include, for example and without limitation, mono-polymer(s), copolymer(s), polymeric blend(s), block polymer(s), block copolymer(s), cross-linked polymer(s), non-cross-linked polymer(s), linear-, branched-, comb-, star-, and/or dendrite-shaped polymer(s), where polymer(s) can be formed into any useful form, for example and without limitation, a hydrogel, a porous mesh, a fiber, woven mesh, or non-woven mesh, such as, for example and without limitation, a non-woven mesh formed by electrodeposition.

Generally, the polymeric components suitable for the scaffold described herein may be any polymer that is biodegradable and biocompatible. By "biodegradable", it is meant that a polymer, once implanted and placed in contact with bodily fluids and/or tissues, will degrade either partially or completely through chemical, biochemical and/or enzymatic processes. Non-limiting examples of such chemical reactions include acid/base reactions, hydrolysis reactions, and enzymatic cleavage.

In certain non-limiting embodiments, the biodegradable polymers may comprise homopolymers, copolymers, and/or polymeric blends comprising, without limitation, one or more of the following monomers: glycolide, lactide, caprolactone, dioxanone, and trimethylene carbonate. In other non-limiting embodiments, the polymer(s) comprise labile chemical moieties, non-limiting examples of which include esters, anhydrides, polyanhydrides, or amides, which can be useful in, for example and without limitation, controlling the degradation rate of the scaffold and/or the release rate of therapeutic agents from the scaffold. Alternatively, the polymer(s) may contain peptides or biomacromolecules as building blocks which are susceptible to chemical reactions once placed in situ. In one non-limiting example, the polymer is a polypeptide comprising the amino acid sequence alanine-alanine-lysine, which confers enzymatic lability to the polymer. In another non-limiting embodiment, the polymer composition may comprise a biomacromolecular component derived from an ECM. For example, the polymer composition may comprise the biomacromolecule collagen so that collagenase, which is present in situ, can degrade the collagen.

The polymer components may be selected so that they degrade in situ on a timescale that is similar to an expected rate of healing of the wound or tissue. Non-limiting examples of in situ degradation rates include between one week and one year or increments therebetween for instance, between two weeks and 10 months, and between one month and six month.

The polymeric components used to make the devices disclosed herein are preferably biocompatible. By "biocompatible," it is meant that a polymer composition and its normal degradation in vivo products are cytocompatible and are substantially non-toxic and non-carcinogenic in a patient within useful, practical and/or acceptable tolerances. By "cytocompatible," it is meant that the polymer can sustain a population of cells and/or the polymer composition, device, and degradation products, thereof are not cytotoxic and/or carcinogenic within useful, practical and/or acceptable tolerances. For example, the polymer when placed in a human cell culture does not adversely affect the viability, growth, adhesion, and number of cells. In one non-limiting embodiment, the compositions, and/or devices are "biocompatible" to the extent they are acceptable for use in a human patient according to applicable regulatory standards in a given jurisdiction. In another example the biocompatible polymer, when implanted in a patient, does not cause a substantial adverse reaction or substantial harm to cells and tissues in the body, for instance, the polymer composition or device does not cause necrosis or an infection resulting in harm to tissues from the implanted scaffold.

The mechanical properties of a biodegradable elastomeric scaffold can be optimized to operate under the normal strain and stress on the native tissue at the site of implantation. In certain non-limiting embodiments, the mechanical properties of the scaffold are optimized similar to or identical to that of native tissue.

The mechanical properties of the scaffold also may be optimized to be suitable for surgical handling. In certain embodiments the scaffold is a gel and has gel like properties that can be controlled by the degree of hydration. For example, the gel can be a hydrogel and be semi-solid, thus having a three dimensional structure. In another non-limiting embodiment, the scaffold is a flexible sheet and can be sutured to the site. In another, the scaffold is foldable and can be delivered to the site by minimally invasive laparoscopic methods.

Variables that can be optimized include without limitation, the extent of physical cross-linking in a network comprising polymeric components, the ratio of polymeric components within the network, the distribution of molecular weight of the polymeric components, and the method of processing the polymers. Polymers are typically semicrystalline and their physical properties and/or morphology are dependent upon a large number of factors, including monomer composition, polydispersity, average molecular weight, cross-linking, and melting/crystallization conditions. For example, flow and/or shear conditions during cooling of a polymer melt are known to affect formation of crystalline structures in the composition. In one non-limiting embodiment, the scaffold comprises a polymeric component that provides strength and durability to the scaffold, yet is elastomeric so that the mechanical properties of the scaffold are similar to the native tissue surrounding the wound or site in need of tissue regeneration.

The extracellular matrix is useful for promoting cell growth on the elastomeric scaffold, extracting appropriate host cells for construction, remodeling, and/or enhancement of biocompatibility. In one non-limiting embodiment, the biological polymeric component comprises and includes an extracellular matrix-derived material. As used herein, the terms "extracellular matrix" and "ECM" refer to a complex mixture of structural and functional biomolecules and/or biomacromolecules including, but not limited to, structural proteins, specialized proteins, proteoglycans, glycosaminoglycans, and growth factors that surround and support cells within mammalian tissues. By "ECM-derived material" it is meant a composition that is prepared from a natural tissue source or from an in vitro source wherein the ECM is produced by cultured cells and comprises one or more polymeric components (constituents) of native ECM. Additionally, "decellularized" ECM refers to ECM in which the cells have been removed through processes described herein and known in the art.

According to one non-limiting example of the ECM-derived material, ECM is isolated from a vertebrate animal, for example, from a warm blooded mammalian vertebrate animal including, but not limited to, human, monkey, pig, cow, sheep, etc. In one non-limiting embodiment, the ECM is isolated from spinal cord, which may or may not include the dura mater. In another non-limiting embodiment, the ECM includes at least a portion of the dura mater. In certain non-limiting embodiments, the material that serves as the biological component of the scaffold consists primarily (e.g., greater than 70%, 80%, or 90%) of ECM. In another non-limiting embodiment, the biodegradable elastomeric scaffold may contain at least 50% ECM, at least 60% ECM, at least 70% ECM, and at least 80% ECM. In yet another non-limiting embodiment, the biodegradable elastomeric scaffold comprises at least 10% ECM. The ECM material may or may not retain some of the cellular elements that comprised the original tissue. The type of ECM used in the scaffold can vary depending on the intended cell types to be recruited during wound healing or tissue regeneration, the native tissue architecture of the tissue organ to be replaced, the availability of the tissue source of ECM, or other factors that affect the quality of the final scaffold and the possibility of manufacturing the scaffold. For example and without limitation, the ECM may contain both a basement membrane surface and a non-basement membrane surface, which would be useful for promoting the reconstruction of tissue. In certain embodiments, an implantable device can comprise either a smooth basement membrane surface (luminal) or a rough non-basement surface (abluminal).

In one non-limiting embodiment, neural scaffolds are made by first removing the cells from excised CNS tissue and then removing any remaining lipids and DNA. Notably, excised CNS tissue is ensheathed in the dura mater membrane. The membrane can be removed and processed independently of the neural tissue according to the methods disclosed. As a result of the processing methods disclosed herein, a gel can be made from cellular spinal cord material; whereas, processing of acellular dura mater creates a fibrous sheet. Those of ordinary skill in the art recognize that washing steps may be performed at any time in the procedures disclosed herein without substantially changing the composition or function of the tissue.

In certain embodiments the decellularization process comprises incubating the tissue (whether the dura mater, spinal cord parenchymal tissue, or a combination thereof) in a solution of non-ionic detergent. Non-ionic detergents are capable of lysing cells and solubilizing the cell membrane as well as many of the cellular components. It is contemplated that various detergents can be used. For example, in certain embodiments, TRITON X-100™ (4-octylphenol polyethoxylate) can be used. However, the methods disclosed herein may be adapted to use any other octylphenol polyethoxylate as well as other detergents such as n-dodecylmaltoside, NONIDET P40™, n-octylglucoside, TWEEN 20, and others.

In certain embodiments, the neural tissue is placed into a cassette. The term "cassette" is intended to mean any three-dimensional hollow structure in which tissue can be place into for processing, such as a tissue cassette or other similar device. As the processed spinal cord parenchymal tissue is a gel, such a cassette helps maintain the tissue structure as well as simplifies handling procedures.

In some embodiments, the neural tissue can be pre-processed. For example, in one embodiment, the tissue is digested using trypsin-EDTA, a protease, before the decellularization process begins. Those of skill in the art recognize that incubation times and temperatures can be varied depending on the amount of tissue. Thus, in certain embodiments, tissue can be digested for 30 minutes at 37° C.

For the decellularization process, tissue can be processed in a non-ionic detergent such as described herein. For example, in one embodiment the tissue can be placed in increasing amounts of TRITON X-100™ solutions. In one embodiment, the tissue can be incubated in 3%-6%-9%, TRITON X-100™ solutions for periods up to 48-72 hours for each percentage. In certain embodiments, the incubation is performed at 4° C. The solutions may be changed as often as needed based on monitoring of the cell cellular removal process.

To remove lipids from the scaffold, an emulsifier can be used. For example, in certain embodiments, lecithin or lecithin-deoxycholate, can be used, although any suitable emulsifier can be used including for example, emulsifying wax, cetearyl alcohol, polysorbate 20, and ceteareth 20, among others. In certain embodiments the tissue is incubated in lecithin overnight at 4° C. and washed with phosphate buffered saline (PBS) three times (15 minutes per wash).

To remove DNA, the tissue can be treated with a DNase such as DNase I. Times and temperatures can be varied according the type of enzyme and the amount of tissues being processed. In one example, the tissue is incubated in a solution of DNase I for 1 hour at room temperature and washed in PBS three times for 15 minutes at room temperature.

Depending on the intended use of the scaffold, the tissue can be washed in deionized water. In some embodiments the tissue is washed in deionized water three times for 15 minutes at room temperature The ECM can be sterilized by any of a number of standard methods without loss of function. For example and without limitation, the material can be sterilized by propylene oxide or ethylene oxide treatment, gamma irradiation treatment (0.05 to 4 mRad), gas plasma sterilization, peracetic acid sterilization, ethanol sterilization, or electron beam treatment. Treatment with glutaraldehyde results in sterilization as well as increased cross-linking of the ECM. This treatment substantially alters the material such that it is slowly resorbed or not resorbed at all and incites a different type of host remodeling, which more closely resembles scar tissue formation or encapsulation rather than constructive remodeling. If desired, cross-linking of the protein material within the ECM can also be induced with, for example and without limitation, carbodiimide isocyanate treatments, dehydrothermal methods, and photooxidation methods. In one non-limiting embodiment, the ECM is disinfected by overnight gamma irradiation treatment with a total exposure of 2 mRad. The ECM-derived material may be further processed by optional drying, desiccation, lyophilization, freeze drying, and/or glassification. The ECM-derived material optionally can be further digested or processed, for example and without limitation by hydration, acidification, alkalinization, enzymatic treatment with, for example and without limitation, trypsin or chondroitinase, and neutralization.

The biodegradable elastomeric scaffolds as described herein may take many different forms. In one non-limiting embodiment, the scaffold is substantially planar (having much greater dimension in two dimensions and a substantially smaller dimension in a third, comparable to bandages, gauze, and other substantially flexible, flat items). In another non-limiting embodiment, the biodegradable elastomeric scaffold comprises a non-woven fibrous article formed by electrodeposition of a suspension containing the synthetic polymeric component and the biological polymeric component. In yet another non-limiting embodiment, the biodegradable elastomeric scaffold comprises a porous composite formed by thermally induced phase separation. The biodegradable elastomeric scaffold can also have three-dimensional shapes useful for treating wounds and tissue deficiencies, such as plugs, rings, wires, cylinders, tubes, or disks.

The biodegradable elastomeric scaffolds may be porous. Porosity may be accomplished by a variety of methods. Although the biodegradable elastomeric scaffolds may be porous or non-porous, it is often advantageous to use a process that produces a porous elastomeric scaffold. Non-limiting examples of such processes include solvent casting/salt leaching, electrodeposition, and thermally induced phase separation. In other examples, porosity may be accomplished by creating a mesh of fibers, such as by the aforementioned electrodeposition or by any suitable method of producing a woven or non-woven fiber matrix. As used herein, the term "porosity" refers to a ratio between a volume of all the pores within the polymer composition and a volume of the whole polymer composition. For instance, a polymer composition with porosity of 85% would have 85% of its volume containing pores and 15% of its volume containing the polymer. In certain non-limiting embodiments, the porosity of the scaffold is at least 60%, 65%, 70%, 75%, 80%, 85%, or 90%, or increments therebetween. In another non-limiting embodiment, the average pore size of the scaffold is between 0.1 and 300 microns, including increments therebetween. For example and without limitation, a biodegradable elastomeric scaffold that acts as a barrier to bacteria and other pathogens may have an average pore size of less than 0.5 microns or less than 0.2 microns. When the scaffold is to be manufactured by electrodeposition, it is often advantageous to adjust the pore size or degree of porosity by varying the polymer concentration of the electrodeposition solution or by varying the spinning distance from the nozzle to the target. For example and without limitation, the average pore size may be increased by increasing the amount of polymeric components within the suspension used for electrodeposition, which results in larger fiber diameters and therefore larger pore sizes. In another non-limiting example, the average pore size can be increased by increasing spinning distance from the nozzle to the target, which results in less adherence between fibers and a looser matrix.

In certain non-limiting embodiments, the biodegradable elastomeric scaffold is made by using solvent casting and salt leaching. This method involves dissolving the polymeric components that constitute the scaffold into a suitable organic solvent and then casting the solution into a mold containing small particles of predetermined size (known as porogens). Examples of suitable porogens include inorganic salts, crystals of saccharose, gelatin spheres or paraffin spheres. By adjusting the porogen size and/or the ratio of porogen to solvent, the porosity of the final elastomeric scaffold may be adjusted. After casting, the solvent is evaporated, and the resulting polymer composition is immersed into a second solvent that dissolves the porogen, but not the polymer, to produce a porous, sheet-like structure.

In other non-limiting embodiments, electrodeposition is used to fabricate the elastomeric scaffold. The process of electrodeposition involves placing a polymer-containing fluid (for example, a polymer solution, a polymer suspension, or a polymer melt) in a reservoir equipped with a small orifice, such as a needle or pipette tip and a metering pump. One electrode of a high voltage source is also placed in electrical contact with the polymer-containing fluid or orifice, while the other electrode is placed in electrical contact with a target (typically a collector screen or rotating mandrel). During electrodeposition, the polymer-containing fluid is charged by the application of high voltage to the solution or orifice (for example, about 3-15 kV) and then forced through the small orifice by the metering pump that provides steady flow. While the polymer-containing fluid at the orifice normally would have a hemispherical shape due to surface tension, the application of the high voltage causes the otherwise hemispherically shaped polymer-containing fluid at the orifice to elongate to form a conical shape known as a Taylor cone. With sufficiently high voltage applied to the polymer-containing fluid and/or orifice, the repulsive electrostatic force of the charged polymer-containing fluid overcomes the surface tension and a charged jet of fluid is ejected from the tip of the Taylor cone and accelerated towards the target, which typically is biased between −2 to −10 kV. Optionally, a focusing ring with an applied bias (for example, 1-10 kV) can be used to direct the trajectory of the charged jet of polymer-containing fluid. As the charged jet of fluid travels towards the biased target, it undergoes a complicated whipping and bending motion. If the fluid is a polymer solution or suspension, the solvent typically evaporates during mid-flight, leaving behind a polymer fiber on the biased target. If the fluid is a polymer melt, the molten polymer cools and solidifies in mid-flight and is collected as a polymer fiber on the biased target. As the polymer fibers accumulate on the biased target, a non-woven, porous mesh is formed on the biased target. The properties of the electrodeposited elastomeric scaffolds can be tailored by varying the electrodeposition conditions. For example, when the biased target is relatively close to the orifice, the resulting electrodeposited mesh tends to contain unevenly thick fibers, such that some areas of the fiber have a "bead-like" appearance. However, as the biased target is moved further away from the orifice, the fibers of the non-woven mesh tend to be more unifoiin in thickness. Moreover, the biased target can be moved relative to the orifice. In certain non-limiting embodiments, the biased target is moved back and forth in a regular, periodic fashion, such that fibers of the non-woven mesh are substantially parallel to each other. When this is the case, the resulting non-woven mesh may have a higher resistance to strain in the direction parallel to the fibers, compared to the direction perpendicular to the fibers. In other non-limiting embodiments, the biased target is moved randomly relative to the orifice, so that the resistance to strain in the plane of the non-woven mesh is isotropic. The properties of the electrodeposited elastomeric scaffold may also be varied by changing the magnitude of the voltages applied to the electrodeposition system. In one non-limiting embodiment, the electrodeposition apparatus includes an orifice biased to 12 kV, a target biased to −7 kV, and a focusing ring biased to 3 kV. Moreover, a useful orifice diameter is 0.047" (I.D.) and a useful target distance is about 23 cm. Other electrodeposition conditions that can be varied include, for example and without limitation, the feed rate of the polymer solutions, the solution concentrations, and the polymer molecular weight. Non-limiting examples of useful range of high-voltage to be applied to the polymer suspension is from 0.5 to 30 kV, from 5 to 25 kV, and from 10 to 15 kV.

In another non-limiting embodiment, thermally induced phase separation (TIPS) is used to fabricate the biodegradable elastomeric scaffold. This method involves dispersing the polymeric components in a solvent (for example and without limitation, DMSO-dimethyl sulfoxide) and then casting, for example by injecting or otherwise placing the composition into a mold. The mold can have any useful shape, such as a sheet or net. In a typical TIPS fabrication process, a pre-formed mold is cooled to low temperature (for example and without limitation-80° C.), which causes the polymeric components to separate out of the solvent. The mold is then transferred to ethanol to extract the DMSO.

Fabrication and modification of the biodegradable elastomeric scaffold can comprise multiple steps using multiple techniques using polymer compositions that are the same or different. In one non-limiting example, TIPS is used to fabricate the biodegradable elastomeric scaffold and electrodeposition is used to form a fiber coating onto or around the scaffold. In another non-limiting example, solvent casting/salt leaching is used to fabricate the biodegradable elastomeric scaffold and electrodeposition is used to form a fiber coating onto or around the scaffold. The electrodeposition solution can contain one or more of any polymeric components, including synthetic polymeric components, biological polymeric components, or mixtures of both. The fiber coating formed by electrodeposition can be coated onto or around the entire scaffold or portions of the scaffold.

After fabricating the biodegradable elastomeric scaffold, the planar or three-dimensional surface of the scaffold may be functionally modified (functionalized) for any purpose, such as, without limitation, to promote cellular adhesion and migration onto and/or into the scaffold. In one non-limiting example, the surface is first treated to introduce a reactive group on the surface by any useful process, such as one of the many processes known in the art. Second, the activated surface is reacted with an adhesion-promoting peptide or group. The reactive group on the surface can be, for example and without limitation, a hydroxyl group or an amine group. In one embodiment, radio-frequency glow discharge is used to produce plasma containing ammonia gas and amine groups are introduced to the surface by treatment with the plasma. In another embodiment, radio-frequency glow discharge is used to introduce hydroxyl groups to the surface by treatment with plasma.

The activated surface can be modified with an adhesion-promoting oligopeptide to promote cellular ingrowth into and/or onto the scaffold. Non-limiting examples of adhesion-promoting oligopeptides include: RGD or RGDS (SEQ ID NO.: 1), a recognition site for fibronectin, vitronectin, fibrinogen, von Willebrand factor, and collagen; LDV, REDV (SEQ ID NO.: 2), PHSRN (SEQ ID NO.: 3), and KNEED (SEQ ID NO.: 4), which are recognition sites for fibronectin; YIGSR (SEQ ID NO.: 5) and IKVAV (SEQ ID NO.: 6), which are recognition sites for laminin; and DGEA (SEQ ID NO.: 7), a recognition site for collagen.

In one specific non-limiting embodiment, the scaffold is functionalized to present the peptide RGDS (SEQ ID NO.: 1) on its surface. First, the surface is treated with radio-frequency glow discharge containing ammonia gas to introduce amine groups. Ammonia-containing gas is generated by connecting a flask containing ammonium hydroxide (30 wt % solution) to the glow discharge reactor and maintaining pressure at $3 \times 10^{-3}$ Torr. The surface is further treated with 1,4-diisocyanatobutane to provide a reactive isocyanate group. Next, RGDS (SEQ ID NO.: 1) is attached to the activated surface. The activated surface is immersed in a solution of 20 μg/mL RGDS (SEQ ID NO.: 1) in PBS for 10 hours and then rinsed with PBS.

One or more of therapeutic agents can be introduced into the biodegradable elastomeric scaffold by any useful method, such as, without limitation absorption, adsorption, deposition, admixture with a polymer composition used to manufacture the scaffold and linkage of the agent to a component of the scaffold. In one non-limiting example, the therapeutic agent is introduced into a backbone of a polymer used in the scaffold. By adding the therapeutic agent to the elastomeric polymer itself, the rate of release of the therapeutic agent may be controlled by the rate of polymer degradation. In another non-limiting example, the therapeutic agent is introduced when the scaffold is being made. For instance, during a solvent casting or TIPS process, the therapeutic agent can be added to the solvent with the polymer in the pre-formed mold. During an electrodeposition process, the therapeutic agent can be electrosprayed onto the polymer being spun. In yet another non-limiting example, the therapeutic agent is introduced into the scaffold after the patch is made. For instance, the scaffold may be "loaded" with therapeutic agent(s) by using static methods. For instance, the scaffold can be immersed into a solution containing the therapeutic agent, permitting the agent to absorb into and/or adsorb onto the scaffold. The scaffold may also be loaded by using dynamic methods. For instance, a solution containing the therapeutic agent can be perfused or electrodeposited into the scaffold. In another instance, a therapeutic agent can be added to the biodegradable elastomeric scaffold before it is implanted in the patient.

Therapeutic agents within the biodegradable elastomeric scaffold can be used in any number of ways. In one non-limiting embodiment, a therapeutic agent is released from the scaffold. For example and without limitation, anti-inflammatory drugs are released from the scaffold to decrease an immune response. In another non-limiting embodiment, a therapeutic agent is intended to substantially remain within the scaffold. For example and without limitation, chemoattractants are maintained within the scaffold to promote cellular migration and/or cellular infiltration into the scaffold.

In one non-limiting embodiment, the biodegradable elastomeric scaffolds release therapeutic agents when the polymeric components degrade within the patient's body. For example and without limitation, the individual building blocks of the polymers may be chosen such that the building blocks themselves provide a therapeutic benefit when released in situ through the degradation process. In one non-limiting embodiment, one of the polymer building blocks is putrescine, which has been implicated as a substance that causes cell growth and cell differentiation.

In another non-limiting embodiment, at least one therapeutic agent is added to the biodegradable elastomeric scaffold before it is implanted in the patient. Generally, the therapeutic agents include any substance that can be coated on, embedded into, absorbed into, adsorbed onto, or otherwise attached to or incorporated onto or into the biodegradable elastomeric scaffold that would provide a therapeutic benefit to a patient. Non-limiting examples of such therapeutic agents include antimicrobial agents, growth factors, emollients, retinoids, and topical steroids. Each therapeutic agent may be used alone or in combination with other therapeutic agents. For example and without limitation, a biodegradable elastomeric scaffold comprising neurotrophic agents or cells that express neurotrophic agents may be applied to a wound that is near a critical region of the central nervous system, such as the spine. Alternatively, the therapeutic agent may be blended with the polymer while the polymer is being processed. For example, the therapeutic agent may be dissolved in a solvent (e.g., DMSO) and added to the polymer blend during processing. In another embodiment, the therapeutic agent is mixed with a carrier polymer (e.g., polylactic-glycolic acid microparticles) which is subsequently processed with an elastomeric polymer. By blending the therapeutic agent with a carrier polymer or elastomeric polymer itself, the rate of release of the therapeutic agent may be controlled by the rate of polymer degradation.

In certain non-limiting embodiments, the therapeutic agent is a growth factor, such as a neurotrophic or angiogenic factor, which optionally may be prepared using recombinant techniques. Non-limiting examples of growth factors include basic fibroblast growth factor (bFGF), acidic fibroblast growth factor (aFGF), vascular endothelial growth factor (VEGF), hepatocyte growth factor (HGF), insulin-like growth factors 1 and 2 (IGF-1 and IGF-2), platelet derived growth factor (PDGF), stromal derived factor 1 alpha (SDF-1 alpha), nerve growth factor (NGF), ciliary neurotrophic factor (CNTF), neurotrophin-3, neurotrophin-4, neurotrophin-5, pleiotrophin protein (neurite growth-promoting factor 1), midkine protein (neurite growth-promoting factor 2), brain-derived neurotrophic factor (BDNF), tumor angiogenesis factor (TAF), corticotrophin releasing factor (CRF), transforming growth factors α and β (TGF-α and TGF-β), interleukin-8 (IL-8), granulocyte-macrophage colony stimulating factor (GM-CSF), interleukins and interferons. Commercial preparations of various growth factors, including neurotrophic and angiogenic factors, are available from R & D Systems, Minneapolis, Minn.; Biovision, Inc, Mountain View, Calif.; ProSpec-Tany TechnoGene Ltd., Rehovot, Israel; and Cell Sciences®, Canton, Mass.

Methods of promoting wound healing or tissue generation or regeneration in a patient also are provided. The methods comprise; without limitation, implanting an elastomeric scaffold as described herein at or near a site for wound healing or tissue generation or regeneration in the patient. In any such method, the elastomeric scaffold may comprise a therapeutic agent as described herein.

In certain non-limiting embodiments, the therapeutic agent is an antimicrobial agent, such as, without limitation, isoniazid, ethambutol, pyrazinamide, streptomycin, clofazimine, rifabutin, fluoroquinolones, ofloxacin, sparfloxacin, rifampin, azithromycin, clarithromycin, dapsone, tetracycline, erythromycin, ciprofloxacin, doxycycline, ampicillin, amphotericin B, ketoconazole, fluconazole, pyrimethamine, sulfadiazine, clindamycin, lincomycin, pentamidine, atovaquone, paromomycin, diclazaril, acyclovir, trifluorouridine, foscarnet, penicillin, gentamicin, ganciclovir, iatroconazole, miconazole, Zn-pyrithione, and silver salts such as chloride, bromide, iodide and periodate.

In certain non-limiting embodiments, the therapeutic agent is an anti-inflammatory agent, such as, without limitation, a NSAID, such as salicylic acid, indomethacin, sodium indomethacin trihydrate, salicylamide, naproxen, colchicine, fenoprofen, sulindac, diflunisal, diclofenac, indoprofen, sodium salicylamide; an anti-inflammatory cytokine; an anti-inflammatory protein; a steroidal anti-inflammatory agent; or an anti-clotting agents, such as heparin. Other drugs that may promote wound healing and/or tissue regeneration may also be included.

In certain non-limiting embodiments, the therapeutic agent comprises cells that are added to the biodegradable elastomeric scaffold before or at the time of implantation. In such embodiments, it is often advantageous to use a porous biodegradable elastomeric scaffold, so that the cells may be incorporated into the porous structure of the scaffold (a condition referred to as "microintegration"). In this way, most of the cells will have a tendency to be trapped or otherwise contained within the porous structure of the scaffold. The cells that are microintegrated may remain after the biodegradable elastomeric scaffold has fully disintegrated within the patient. However, the microintegrated cells may also be merely cells that act as precursors to the final tissue that is formed when the biodegradable elastomeric scaffold has fully degraded.

Cells may be autologous (obtained from the patient to receive the scaffold), from an allogeneic or xenogeneic source or from any useful cell line, such as, without limitation, stem cells that are capable of cellular growth, remodeling, and/or differentiation. By way of example only, the cells that may be incorporated onto or into the biodegradable scaffold include stem cells, precursor cells, smooth muscle cells, skeletal myoblasts, myocardial cells, endothelial cells, and genetically modified cells. Various commercially available cell lines include Clonetics® Primary Cell Systems (Lonza Group, Inc., Switzerland), ATCC.

Cells may be microintegrated with the biodegradable elastomeric scaffold using a variety of methods. For example and without limitation, the elastomeric scaffold may be placed in a suitable growth medium for the cells of interest, and then exposed to the cells. The cells are allowed to proliferate on the surface and interstices of the elastomeric scaffold. The elastomeric scaffold is then removed from the growth medium, washed if necessary, and implanted. Alternatively, the cells may be placed in a suitable buffer or liquid growth medium and drawn through the scaffold by using vacuum filtration. In another non-limiting embodiment, the cells of interest are dissolved into an appropriate solution (e.g., a growth medium or buffer) and then sprayed onto a biodegradable elastomeric scaffold while the scaffold is being formed by electrodeposition. In yet another non-limiting embodiment, the cells are placed in a solution that is biased and then electrosprayed onto the biodegradable elastomeric scaffold while it is being electrodeposited. By way of example only, the cells that may be incorporated on or into the biodegradable scaffold include chondrocytes, stem cells, precursor cells, smooth muscle cells, skeletal myoblasts, myocardial cells, endothelial cells, and genetically modified cells.

In one non-limiting embodiment, the genetically modified cells are capable of expressing a therapeutic substance, such as a growth factor. Cells can be modified by any useful method in the art. For example and without limitation, the therapeutic agent is a growth factor that is released by cells transfected with cDNA encoding for the growth factor. Therapeutic agents that can be released from cells include, without limitation, a neurotrophic factor, such as nerve growth factor, brain-derived neurotrophic factor, neurotrophin-3, neurotrophin-4, neurotrophin-5, and ciliary neurotrophic factor; a growth factor, such as basic fibroblast growth factor (bFGF), acidic fibroblast growth factor (aFGF), vascular endothelial growth factor (VEGF), hepatocyte growth factor (HGF), insulin-like growth factors (IGF), platelet derived growth factor (PDGF), transforming growth factor-beta (TGF-β), pleiotrophin protein (neurite growth-promoting factor 1), and midkine protein (neurite growth-promoting factor 2); an anti-inflammatory cytokine; and an anti-inflammatory protein. The cells may be autologous, allogeneic, etc.

In addition to providing biodegradable elastomeric scaffolds as described above, methods of using such elastomeric scaffolds are encompassed herein. Generally, a biodegradable elastomeric scaffold can be implanted by using any suitable medical procedure that facilitates use of the scaffold to provide a therapeutic benefit. As used herein, the terms "implanted" and "implantation" and like terms refer to an act of delivering a biodegradable elastomeric scaffold to a site within the patient. The site of implantation in a patient typically is "at or near a site for wound healing or tissue generation or regeneration in the patient," meaning the scaffold-containing device is implanted in, on, onto, adjacent to or in proximity to a desired site of delivery to facilitate healing and/or tissue generation or regeneration to repair an injury or defect in the patient and/or to achieve a desired effect in the patient, such as wound drainage. The delivery method may also include minimally invasive methods such as by catheter based technology or by needle injection. The patient may be human or animal. The scaffold may be delivered by any surgical procedure, including minimally invasive techniques, such as laparoscopic surgery, as well as invasive techniques such as thoracic surgery and fasciotomy. In certain non-limiting embodiments, the elastomeric scaffolds are used as surgical fabrics. The biodegradable elastomeric scaffold may be implanted alone or implanted in conjunction with surgical fasteners, such as sutures, staples, adhesives, screws, pins, and the like. Additionally, biocompatible adhesives, such as, without limitation, fibrin-based glue may be used to fasten the elastomeric scaffolds as well.

In yet another non-limiting embodiment, the scaffold can be in the form of a powder or fine particles (for example, formed by shredding a non-woven mesh formed by electrodeposition or TIPS). In these situations, it may be advantageous to derivatize the elastomeric scaffold with therapeutic agents, such as antibiotics or growth factors, prior to insertion into the wound.

EXAMPLES

Example 1

Manufacturing Acellular Spinal Cord and Dura Mater Biological Scaffolds

In one example, porcine spinal cord was obtained. Using forceps, scissors and a scalpel, dura mater was removed from the spinal cord. The inner dura mater surface was scrapped with scalpel blade to remove any debris. The spinal cord and dura were placed in separate containers and treated in the same manner as listed below. The spinal cord was cut either longitudinally or in cross-section (to increase surface area) and placed in a cassette (e.g., safety container to protect 3-D structure of cord throughout process). Optionally tissue was enzymatically treated using trypsin-EDTA for 30 minutes at 37° C. The tissue was incubated in TRITON X-100™ (4-octylphenol polyethoxylate) solutions at 3% for periods up to 2-3 days at 4° C. This step was repeated with a solution of Triton X-100 at 6% and again with a solution of Triton X-100 at 9%. The spinal cord tissue was incubated in lecithin or lecithin-deoxycholate to remove lipids overnight at 4° C. Dura mater was not subjected to this procedure. Tissue was then washed in TRITON X-100 3% or SDS 1% for 1-2 hours. The tissue was rinsed in PBS X 3 for 15 minutes at room temperature. Then the tissue was incubated in a solution of DNase I for 1 hour at room temperature. The tissue was washed in PBS three times for 15 minutes at room temperature. Lastly, the tissue was washed in deionized water three times for 15 minutes at room temperature. The procedure produced a gel-like acellular spinal cord material, and a sheet of acellular dura mater material. Sections of each material were sent for histology to confirm lack of cells. Biocompatibility was tested by culturing the scaffolds with either primary neuronal cells or a neuronal cell line (e.g. PC 12 cell line)

Example 2

Characterization of the Neuronal Scaffolds

Figure 1:
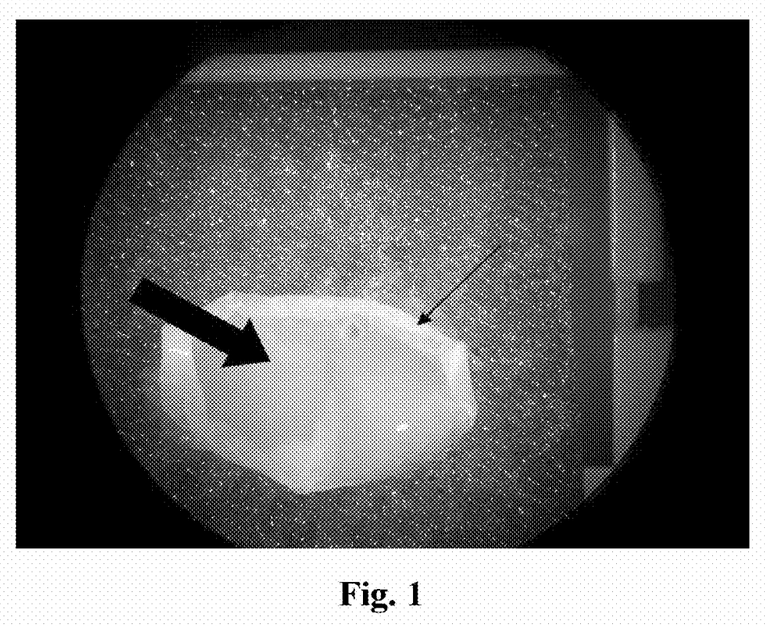
FIG. 1 is a digital image showing the gel-like quality of the spinal cord parenchyma-derived scaffold. The thick arrow indicates the gel-like substance and the thin arrow indicates the pia matter (6×)

Described in this example is the characterization of the neuronal scaffolds. After the last step of the process described in the example 1, the acellular spinal cord parenchyma-derived neuronal scaffold is gel-like. FIG. 1 is a digital image showing the gel-like quality of the scaffold. The thick arrow indicates the gel-like substance and the thin arrow indicates the pia matter.

Figure 2A:
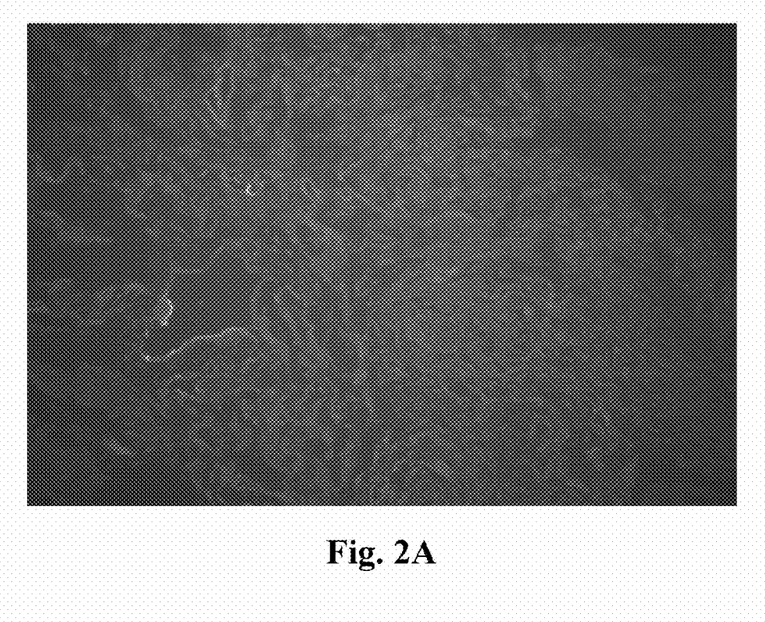
FIGS. 2A-B are fluorescence photomicrographs of the acellular spinal cord parenchyma-derived scaffold showing lack of nuclei and cells within the scaffold, which has been stained with nuclei marker DAPI (200×)
Figure 2B:
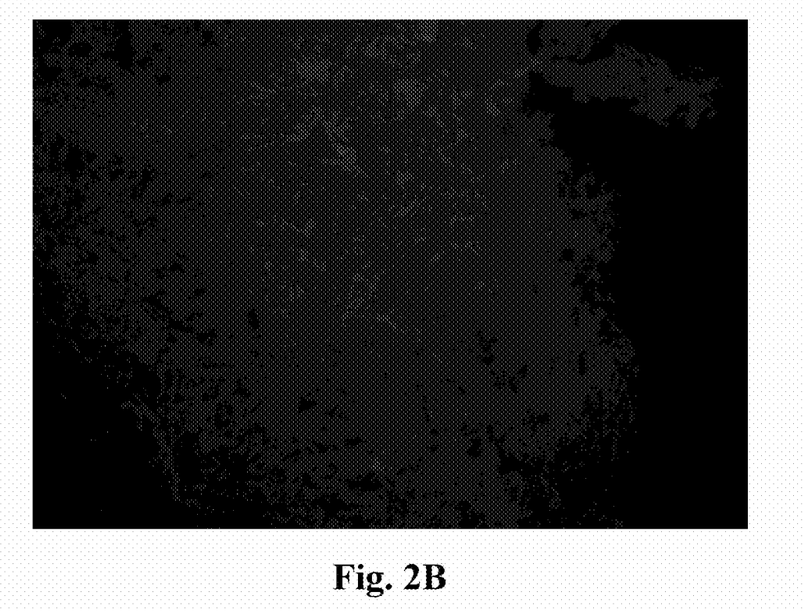
Figure 3:
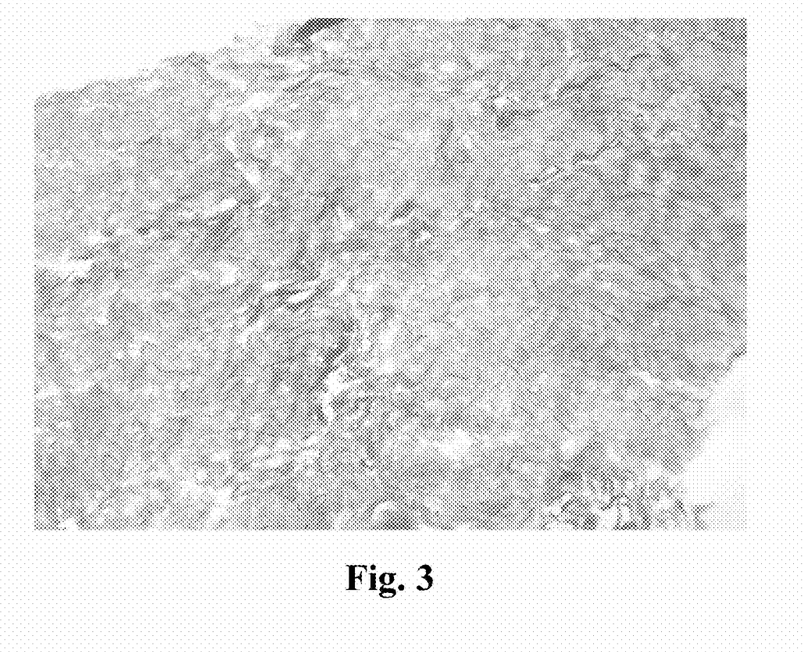
FIG. 3 is a photomicrograph of Masson's trichrome stained acellular spinal cord parenchyma-derived scaffold (200×)
Figure 4A:
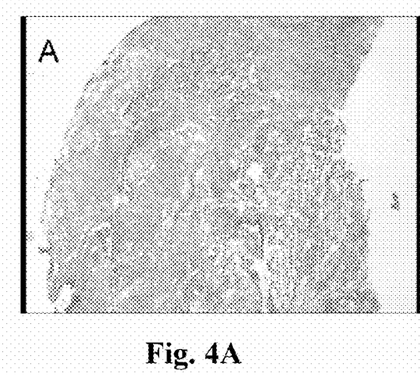
FIG. 4A shows hematoxylin and eosin (H&E) stained acellular porcine spinal cord scaffold (100×).
Figure 4B:
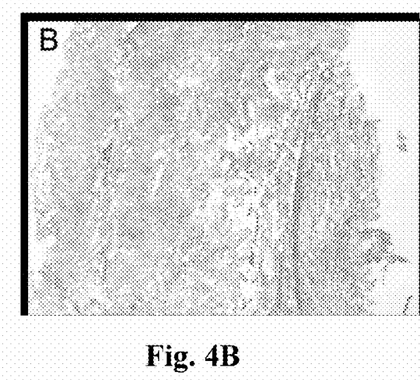
FIG. 4B shows Masson's trichrome stained acellular porcine spinal cord-derived scaffold (100×).
Figure 4C:
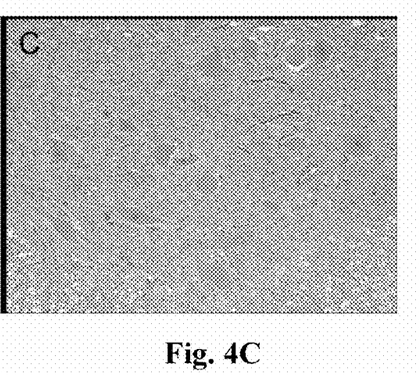
FIG. 4C shows Masson's trichrome stained normal adult porcine spinal cord, grey matter (100×).
Figure 4D:
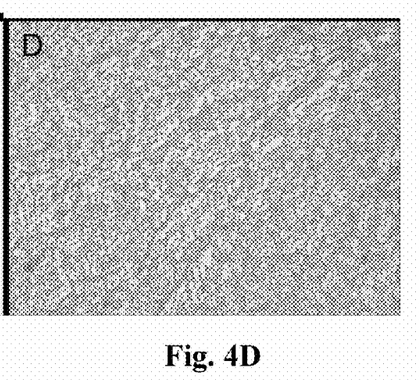
FIG. 4D shows Masson's trichrome stained normal adult porcine spinal cord, white matter (100×)
Figure 8A:
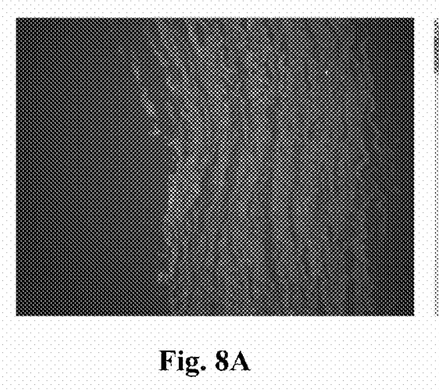
FIG. 8A shows a fluorescence photomicrographs of the acellular dura mater scaffold showing lack of nuclei and cells within the scaffold, which has been stained with nuclei marker DAPI (200×).
Figures 8B, 8D:
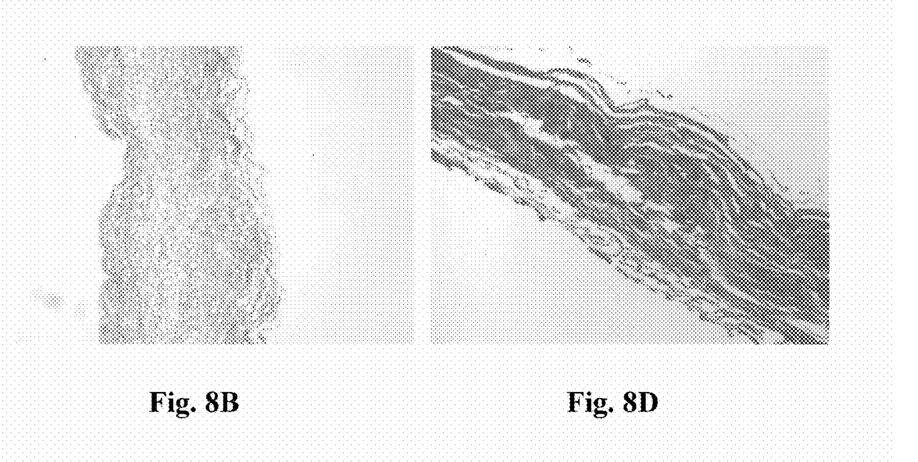
FIG. 8B shows Masson's trichrome stained acellular porcine dura mater scaffold (100×).
FIGS. 8C-8D show Masson's trichrome stained photomicrographs of neuronal cell growth (red) on the acellular dura mater scaffold (blue); photomicrograph magnification: 200× (FIG. 8C) and 400× (FIG. 8D).

After forming the neuronal scaffolds, the scaffold is acellular. Various methods were used to determine whether the scaffold was acellular. First, fluorescent stains, such as DAPI (4',6-diamidino-2-phenylindole), were used to determine whether cells are present. FIGS. 2A-2B and FIG. 8A are fluorescence photomicrographs of the scaffold stained with DAPI, where lack of fluorescence correlated with lack of nuclei and cells within the scaffold. Second, histological stains, such as Masson's trichrome, were also be used. FIG. 3 and FIG. 8B show photomicrographs of Masson's trichrome stained scaffolds, which show that cells are not present within the scaffolds. FIGS. 4A-4D provide comparisons between the acellular spinal cord parenchyma-derived neuronal scaffolds and native adult porcine spinal cord. FIGS. 4A-4B show an acellular porcine spinal cord parenchyma-derived neuronal scaffold that has been stained with hematoxylin and eosin (FIG. 4A) or with Masson's trichrome (FIG. 4B). FIGS. 4C-4D show Masson's trichrome stained grey matter (FIG. 4C) and white matter (FIG. 4D) of a normal adult porcine spinal cord.

Figure 5A:
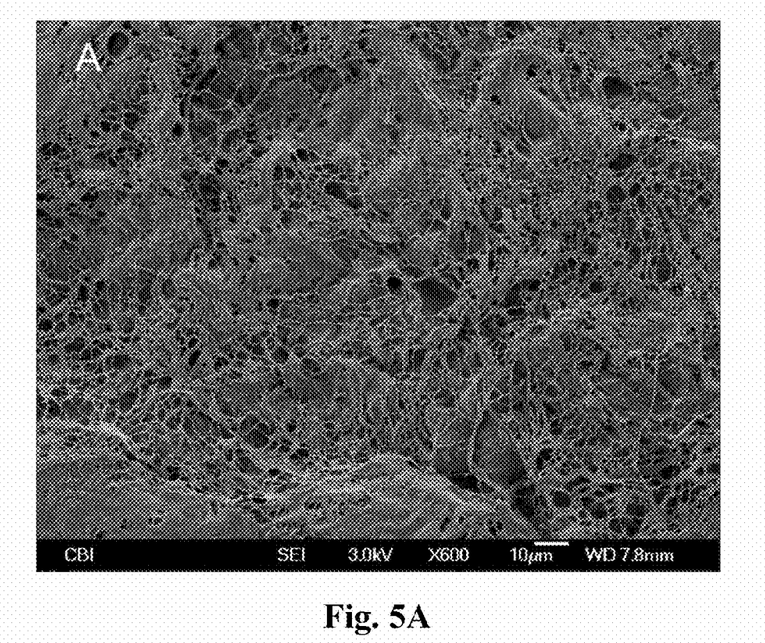
FIG. 5A shows the scaffold at 600× magnification and FIG. 5B shows the scaffold at 2,000× magnification.
Figure 5B:
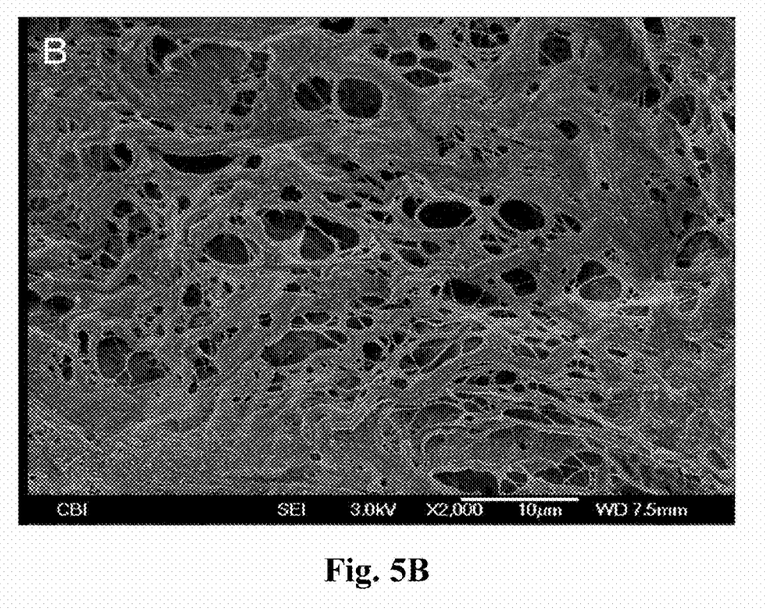

The porosity, topology, and morphology of the scaffold were determined by various methods, including scanning electron microscopy (SEM). Specifically, samples were fixed in 2.5% glutaraldehyde in PBS overnight, rinsed with PBS, 15 min at RT and treated with 1% osmium tetroxide in PBS for 60 minutes at room temperature. The tissue was rinsed again in PBS and processed with sequential ethanol dehydration: 30%, 50%, 70%, 90% for 15 minutes each; 100%×15 min×3. The sample was treated with HMDS (hexamethyldisiazane) for 1 hour at room temperature, removed by HMDS and air-dried overnight. Samples were then sputter coated and scanned FIGS. 5A-5B are scanning electron micrographs of acellular spinal cord parenchyma-derived neuronal scaffold at 600× magnification (FIG. 5A) and at 2,000× magnification (FIG. 5B).

Example 3

Testing for Biocompatibility of the Neuronal Scaffolds

Biocompatibility of the neuronal scaffold was tested by culturing primary neuronal cells and neuronal cell lines on the scaffold. Rat adrenal pheochromocytoma (PC 12) cells were obtained from ATCC (American Type Culture Collections, Manassas, Va.), ATCC catalog number CRL-1721. The PC12 cells were grown in DMEM with 10% heat-inactivated horse serum, 5% fetal bovine serum, 1% penicillin-streptomycin solution (stock solution: 10,000 units penicillin and 10,000 µg streptomycin/ml) in a humidified incubator at 37° C. supplemented with 5% $CO_2$ in plastic cell culture-treated flasks. Cells were not allowed to become more than 50% confluent in culture flasks before sub-culturing. Prior to seeding on neural scaffolds, adherent PC12 cells were trypsinized (5 ml 0.25% trypsin with EDTA/75 sq. cm flask) to release and remove cells from culture flasks. Once cells were non-adherent, the trypsin was neutralized with 20 ml culture medium (containing horse serum and fetal bovine serum). Cells were then centrifuged at 800 g for 5 minutes and the supernatant was removed. Cells were resuspended in 3 ml culture medium and counted using a hemocytometer. A total of $1.5 \times 10^6$ cells were seeded on each neural scaffold (approximately $5 \times 10^5$/square centimeter). Cells were allowed to grow on neural scaffolds for 2 days. The neural scaffold-PC12 biomaterials were fixed in 10% (neutral buffered) formalin for 24 hours, mounted in paraffin, sectioned (5 µm sections), mounted on glass slides, stained (H&E, Masson's trichrome) and coverslipped. These neural scaffold-PC12 cultures were not supplemented with NGF (typically 50 ng/ml), but the growth factor can be added to this cell line to stimulate and evaluate neurite outgrowth.

Figure 6A:
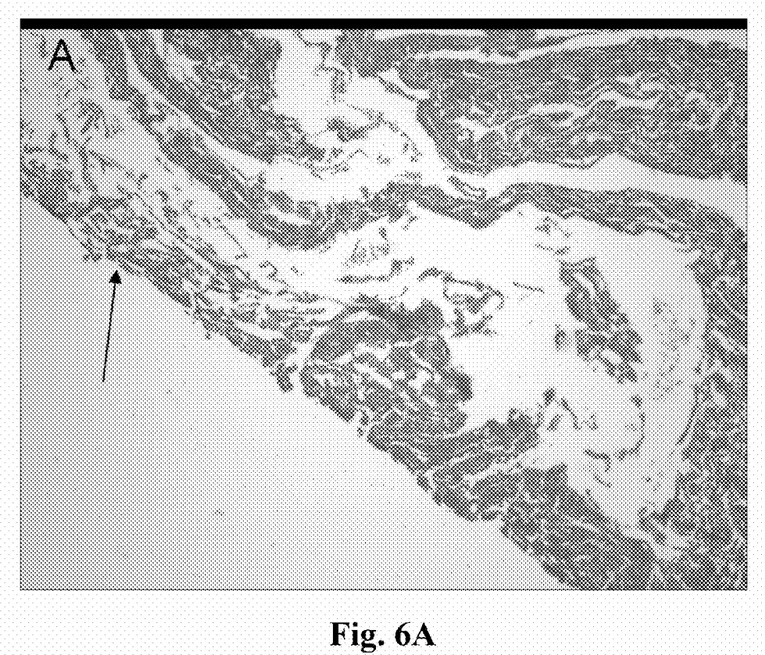
Figure 6B:
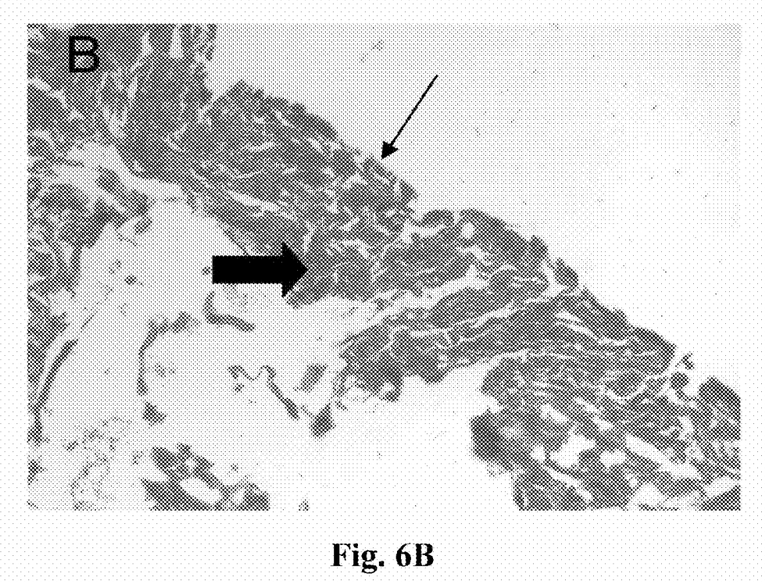
Figure 6C:
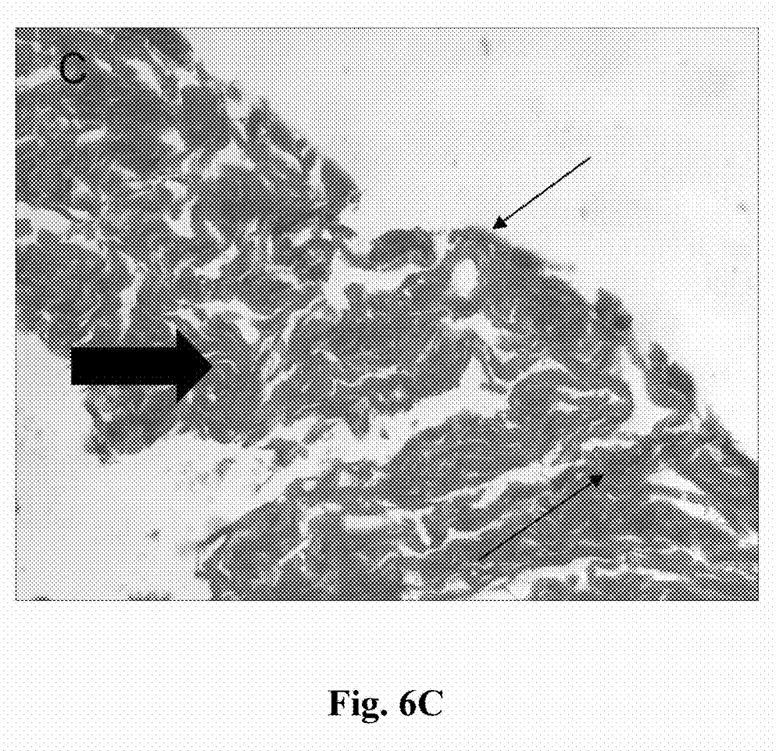
Figure 7A:
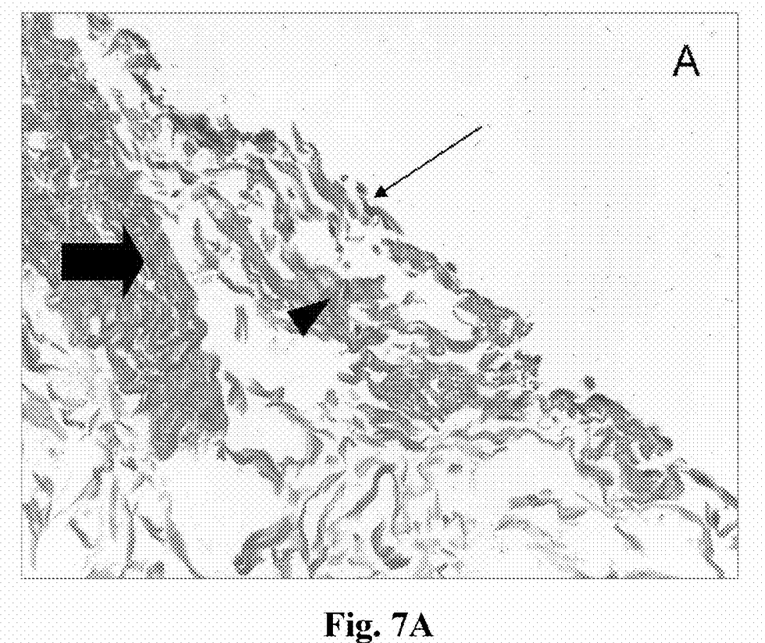
Figure 7B:
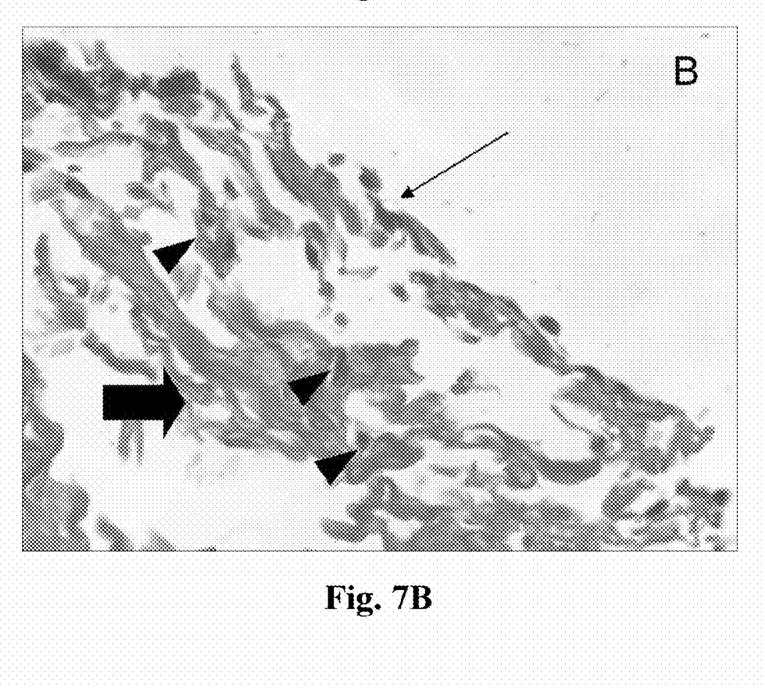
Figure 8C:
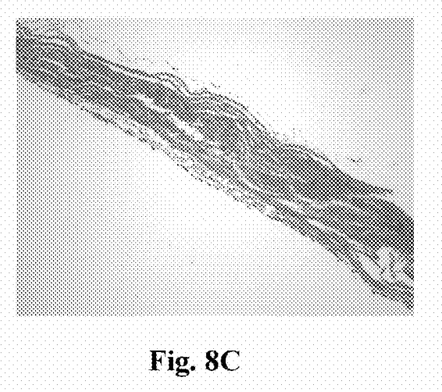

The response of the PC12 cells to the neuronal scaffolds was determined by Masson's trichrome stain. FIGS. 6A-6C and 7A-7B shows photomicrographs of Masson's trichrome stained acellular spinal cord parenchyma-derived neural scaffold implanted with neuronal cells (PC12). FIGS. 6A-6C show neuronal cell growth and migration into this neural scaffold, where neuronal cells (red, thin arrows) grew on and into the scaffold (blue, thick arrows). FIGS. 7A-7B show neuronal cell growth and migration in this scaffold (blue, thick arrows). Neuronal cells grew on the surface of the scaffold (red, thin arrows) and migrated into the scaffold (arrowheads). FIGS. 8C-8D show neuronal cells (red) growing on the surface of the dura mater-derived neural scaffold (blue).

Having described this invention, it will be understood to those of ordinary skill in the art that the same can be performed within a wide and equivalent range of conditions, formulations and other parameters without affecting the scope of the invention or any embodiment thereof.

Having now described the features, discoveries and principles of the invention, the manner in which the neural scaffolds are used and installed, the characteristics of the construction, arrangement and method steps, and the advantageous, new and useful results obtained; the new and useful structures, devices, elements, arrangements, process, parts and combinations are set forth in the appended claims.

What is claimed is:

1. A method of manufacturing a neural scaffold comprising: placing spinal cord tissue that does not comprise dura mater in a cassette; incubating the tissue in a solution comprising a non-ionic surfactant; washing the tissue to remove the non-ionic surfactant; incubating the tissue in a solution comprising an emulsifier; washing the tissue to remove the emulsifier; incubating the tissue in a solution comprising DNase; washing the tissue to remove the DNase; and removing the tissue from the cassette.

2. The method of claim 1, wherein the spinal cord tissue is enzymatically digested in a solution of trypsin-EDTA prior to being incubated in a solution comprising a non-ionic surfactant.

3. The method of claim 2, wherein the spinal cord tissue is enzymatically digested for 30 minutes at 37° C.

4. The method of claim 1, wherein the surfactant is 4-octylphenol polyethoxylate.

5. The method of claim 4, wherein the tissue is incubated for a first period of greater than forty eight hours in a first concentration of 4-octylphenol polyethoxylate.

6. The method of claim 5, wherein the first concentration is 3% by volume.

7. The method of claim 5, where the tissue is incubated for a second period of greater than forty eight hours in a second concentration of 4-octylphenol polyethoxylate.

8. The method of claim 7, wherein the second concentration is 6% by volume.

9. The method of claim 7, where the tissue is incubated for a third period of greater than forty eight hours in a third concentration of 4-octylphenol polyethoxylate.

10. The method of claim 9, wherein the third concentration is 9% by volume.

11. The method of claim 1, wherein the emulsifier is lecithin or lecithin-deoxycholate.

12. The method of claim 11, wherein the tissue is incubated in the solution comprising lecithin or lecithin-deoxycholate for at least 12 hours at 4° C.

13. The method of claim 1, wherein washing the tissue to remove the emulsifier comprises incubating the tissue in a detergent.

14. The method of claim 13, wherein the detergent is 4-oetylphenol polyethoxylate or sodium dodecyl sulfate.

15. The method of claim 14, wherein the 4-octylphenol polyethoxylate is in 3% solution by volume.

16. The method of claim 14, wherein the sodium dodecyl sulfate is in 1% solution by volume.

17. The method of claim 13, wherein the tissue is rinsed in phosphate buffered saline after incubating in detergent.

18. The method of claim 1, wherein the tissue is incubated in DNase for at least one hour at room temperature.

19. The method of claim 18, wherein the tissue is washed in phosphate buffered saline after incubating in DNase.

20. The method of claim 19, wherein the tissue is washed in de-ionized water after being washed in phosphate buffered saline.

21. A product produced by the process of claim 1.

22. A method of treatment for neural injury or disease, comprising grafting the product of claim 20 into a site of disease or injury in a mammal.

* * * * *

UNITED STATES PATENT AND TRADEMARK OFFICE
CERTIFICATE OF CORRECTION

PATENT NO. : 8,685,634 B2  
APPLICATION NO. : 12/718227  
DATED : April 1, 2014  
INVENTOR(S) : Alan V. Boruch Page 1 of 1

It is certified that error appears in the above-identified patent and that said Letters Patent is hereby corrected as shown below:

In The Claims

Column 16, Lines 42-43, Claim 14, delete "4-oetylphenol" and insert -- 4-octylphenol --

Column 16, Line 59, Claim 22, delete "claim 20" and insert -- claim 21 --

Signed and Sealed this  
Ninth Day of December, 2014

Michelle K. Lee  
*Deputy Director of the United States Patent and Trademark Office*